(12) United States Patent
Mehdizadeh

(10) Patent No.: US 7,844,363 B1
(45) Date of Patent: Nov. 30, 2010

(54) VENDING MACHINE APPARATUS TO DISPENSE HERBAL MEDICATIONS AND PRESCRIPTION MEDICINES

(75) Inventor: P. Vincent Mehdizadeh, Beverly Hills, CA (US)

(73) Assignee: PVM International, Inc., West Hills, CA (US)

( * ) Notice: Subject to any disclaimer, the term of this patent is extended or adjusted under 35 U.S.C. 154(b) by 0 days.

(21) Appl. No.: 11/999,385

(22) Filed: Dec. 4, 2007

(51) Int. Cl.
*G06F 17/00* (2006.01)
(52) U.S. Cl. ..................... 700/237; 700/232; 700/244
(58) Field of Classification Search .......... 700/231–244
See application file for complete search history.

(56) References Cited

U.S. PATENT DOCUMENTS 6,874,684 B1 * 4/2005 Denenberg et al. .......... 235/381
7,123,989 B2 * 10/2006 Pinney et al. ............... 700/237
2008/0269947 A1 * 10/2008 Beane et al. ............... 700/237

* cited by examiner

*Primary Examiner*—Gene Crawford
*Assistant Examiner*—Michael K Collins
(74) *Attorney, Agent, or Firm*—Thomas I. Rozsa

(57) ABSTRACT

The present invention relates to the idea of enabling an individual to conveniently purchase herbal medications and prescription medicines from specialized vending machines. The system provides for the individual to be processed through a central database to be certain that the item being purchased has been legally authorized by an appropriate medical authority such as a licensed physician and has provided appropriate verification to confirm that the individual who is receiving the medication is the correct individual. The present invention enables the individual to conveniently purchase the medication from a vending machine.

3 Claims, 6 Drawing Sheets

VENDING MACHINE APPARATUS TO DISPENSE HERBAL MEDICATIONS AND PRESCRIPTION MEDICINES

BACKGROUND OF THE INVENTION

1. Field of the Invention

The present invention relates to the field of vending machines which dispense products therefrom.

2. Description of the Prior Art

In general, vending machines are well known in the prior art. However, while frequently used to dispense numerous different products, because of legal and medical requirements, herbal medications and prescription medicines have not been sold and dispensed through vending machines.

There is a significant need for a safe and legalized system to dispense herbal medications and prescription medicines through vending machines.

SUMMARY OF THE INVENTION

The present invention relates to the idea of enabling an individual to conveniently purchase herbal medications and prescription medicines from specialized vending machines. The system provides for the individual to be processed through a central database to be certain that the item being purchased has been legally authorized by an appropriate medical authority such as a licensed physician and has provided appropriate verification to confirm that the individual who is receiving the medication is the correct individual. The present invention enables the individual to conveniently purchase the medication from a vending machine.

The present invention relates to machines that will contain a variety of box sizes that are to be distributed much like any other vending machines. The difference is the contents which shall be in an array of popular medications. Propecia, Viagra and medical marijuana will all be accessible by prescription. The machine will contain appropriate purchaser verification means and will also be temperature controlled to assure that the medications will be properly stored.

It is therefore an object of the present invention to be able to distribute legal medications through a vending machine operation.

Further novel features and other objects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Defined in detail, the present invention embodies the concept of a vending machine which can distribute legal medical products such as Propecia, Viagra, prescription medicine and herbal medications. In order to be able to obtain such a prescription from the vending machine, the individual must obtain a legal prescription from a licensed medical doctor. The individual will then need to bring the prescription to a legal processing center where the individual will be photographed for I.D. purposes including fingerprinting, visual photographs, provided with a PIN code for each transaction and other critical information about the individual so that this information can be recorded into a central computer database which transmits this machine to one or more vending machines located in various areas.

Figure 1:
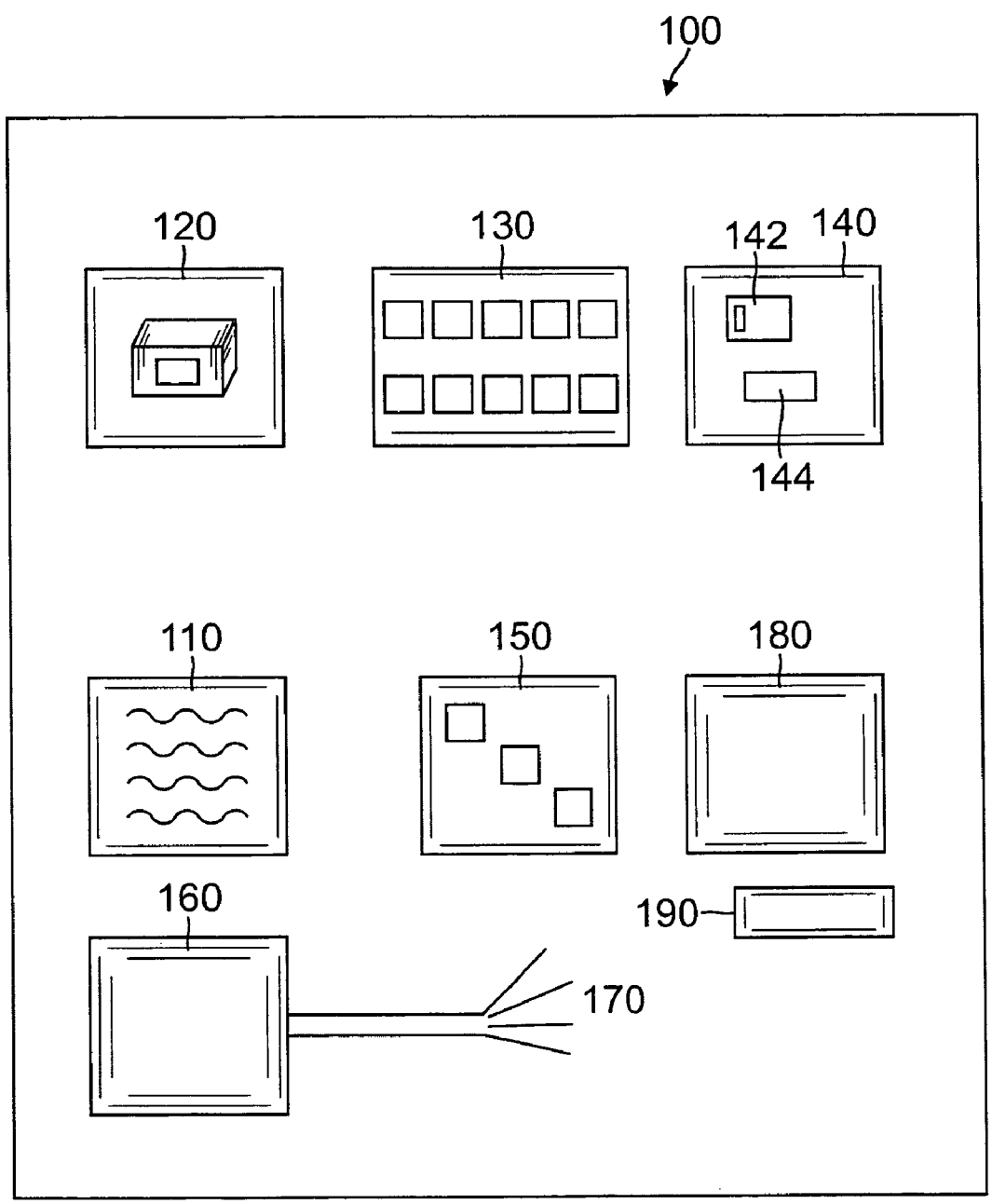
FIG. 1 is a schematic representation of a central processing area where an individual goes to present a prescription and provide critical information about the individual which is then placed into a computer which transmits that information to a vending machine. There are also mechanism for the individual to provide confirmed verification that the individual is the same one who received the prescription and methods for transmitting this information to a central kiosk where the product will be dispensed.
Figure 2:
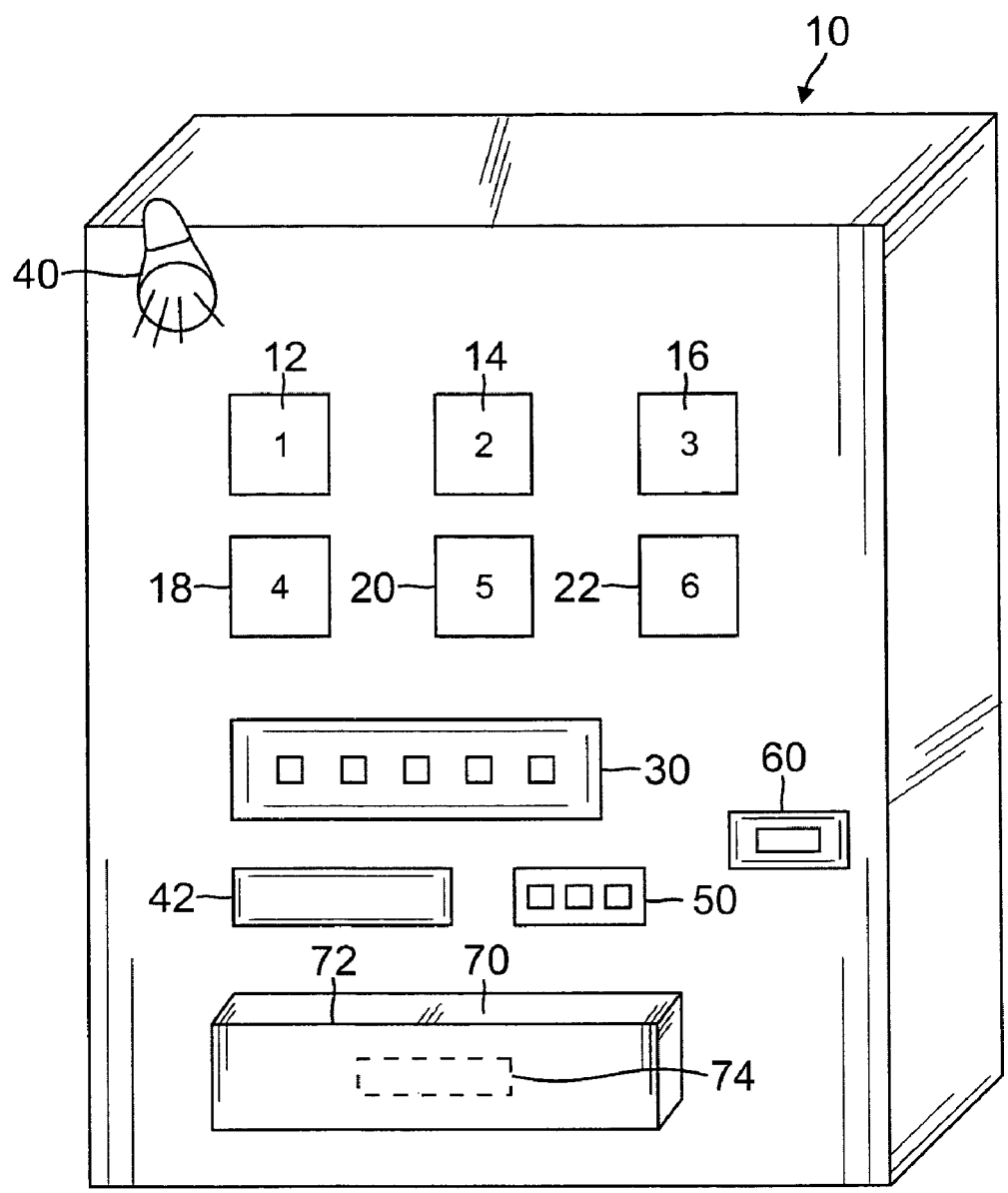
FIG. 2 is a schematic representation of a central kiosk that has a selection mechanism to select a specific medical substance and the quantity and means for the individual to confirm that the individual purchasing the substance is the same individual who is authorized to do so and has paid for it and means to dispense the substance so the individual can retrieve it from the kiosk.
Figure 3:
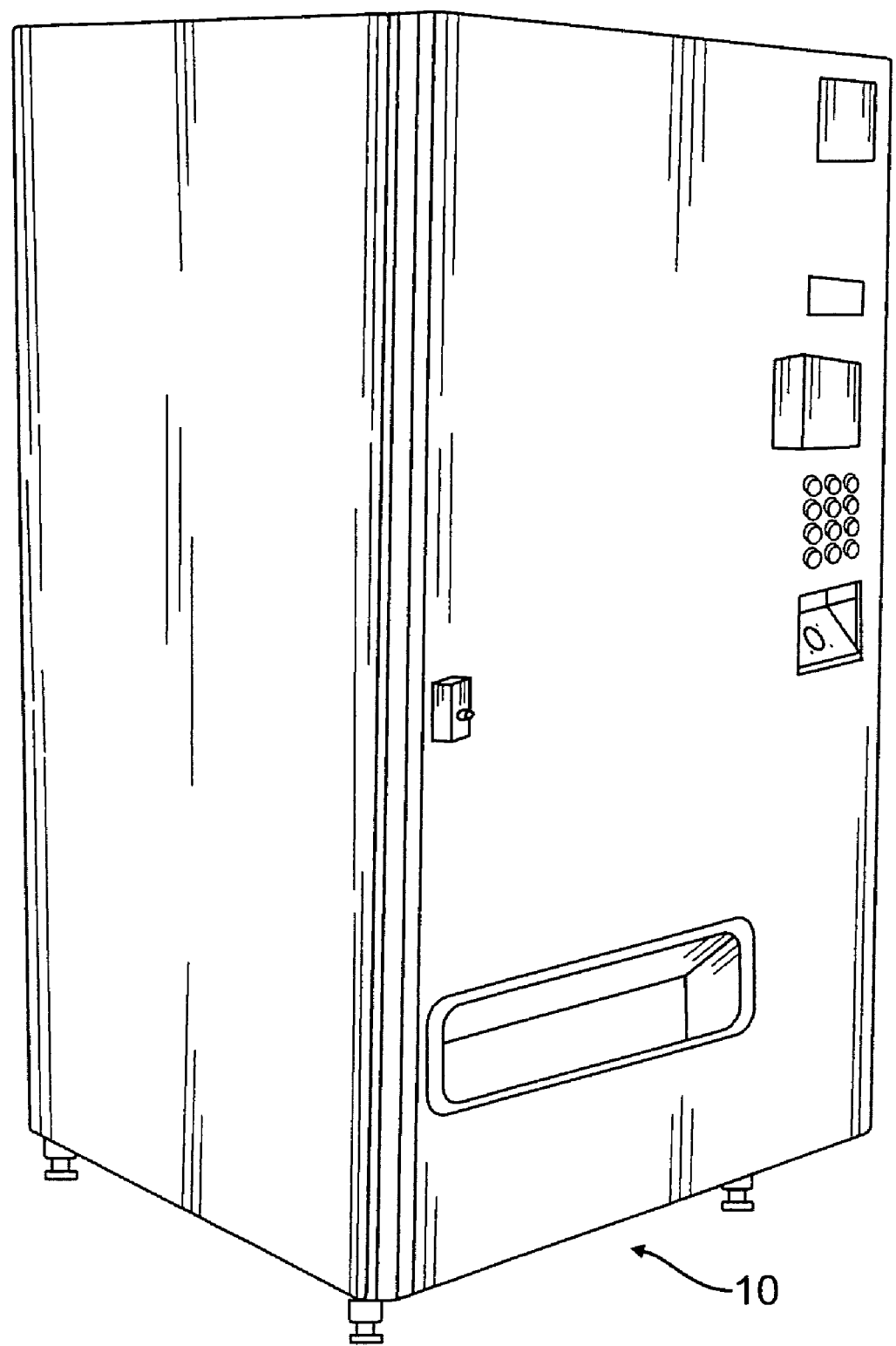
FIG. 3 is a perspective view of one embodiment of the vending machine of the present invention.
Figure 4:
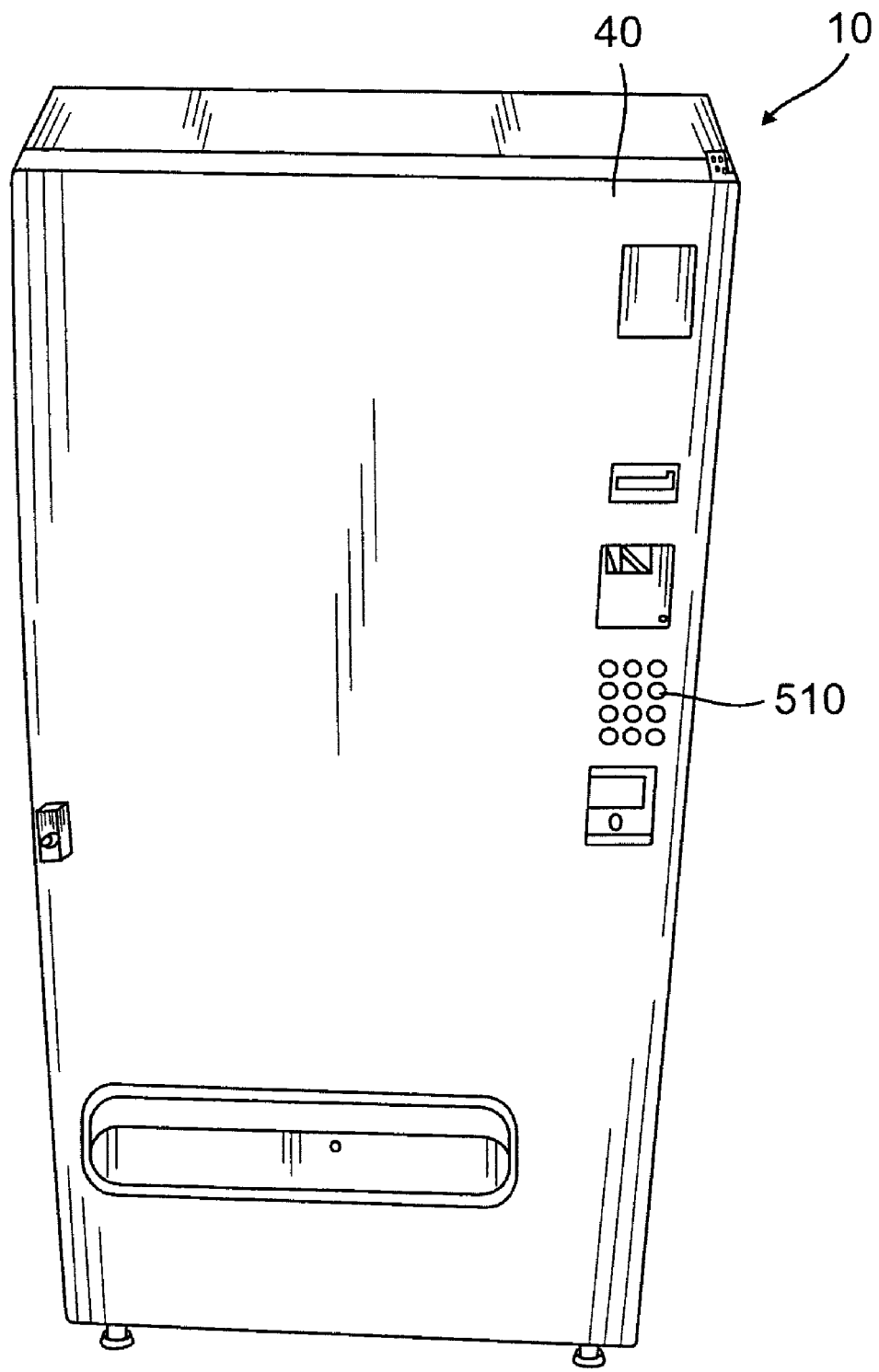
FIG. 4 is a front elevational view of one embodiment of the vending machine of the present invention.

Referring to FIG. 1, there is a central processing area or central processing center 100. At the central processing center, an individual will bring a prescription 110 from a licensed medical doctor which he obtains for a specific prescription for a specific medical substance in a specific medical quantity. The prescription may also contain a certain dosage level for Viagra, Propecia or other medical substance, other prescription medicines or herbal medications. At the processing center the individual will be photographed through a photographic process 120 so that it is clear that the individual who has the prescription is clearly identified. In addition, the individual will be fingerprinted through fingerprint process 130 and will provide further positive identification information 140 such as a driver's license 142 and a credit card 144. The individual will then be provided with a pin code 150 and in the preferred situation the individual will create the PIN Code for the individual so only the individual will know it. Other critical information in addition to the photograph which will be electronically scanned, the fingerprints which will be electronically scanned, the other identification information such as a driver's license and credit card will be electronically scanned, the actual prescription 110 and the pin code will be input into a central processing database 160 which will then send through electronic transmission means 170 the information to each of the specific individual vending kiosks where the prescription can be filled. The individual will preferably pay for the medical substance at the processing center through a payment means 180 which will be either check, credit card, etc. Payment can also be made electronically on-line Optionally, the individual, if it is agreed upon between the central processing center and the individual may pay for the substance at the time the individual goes to the specific vending machine. The individual also has an electronic signature means 190 so the individual can give an electronic signature which will then be confirmed at the vending machine.

Figure 5:
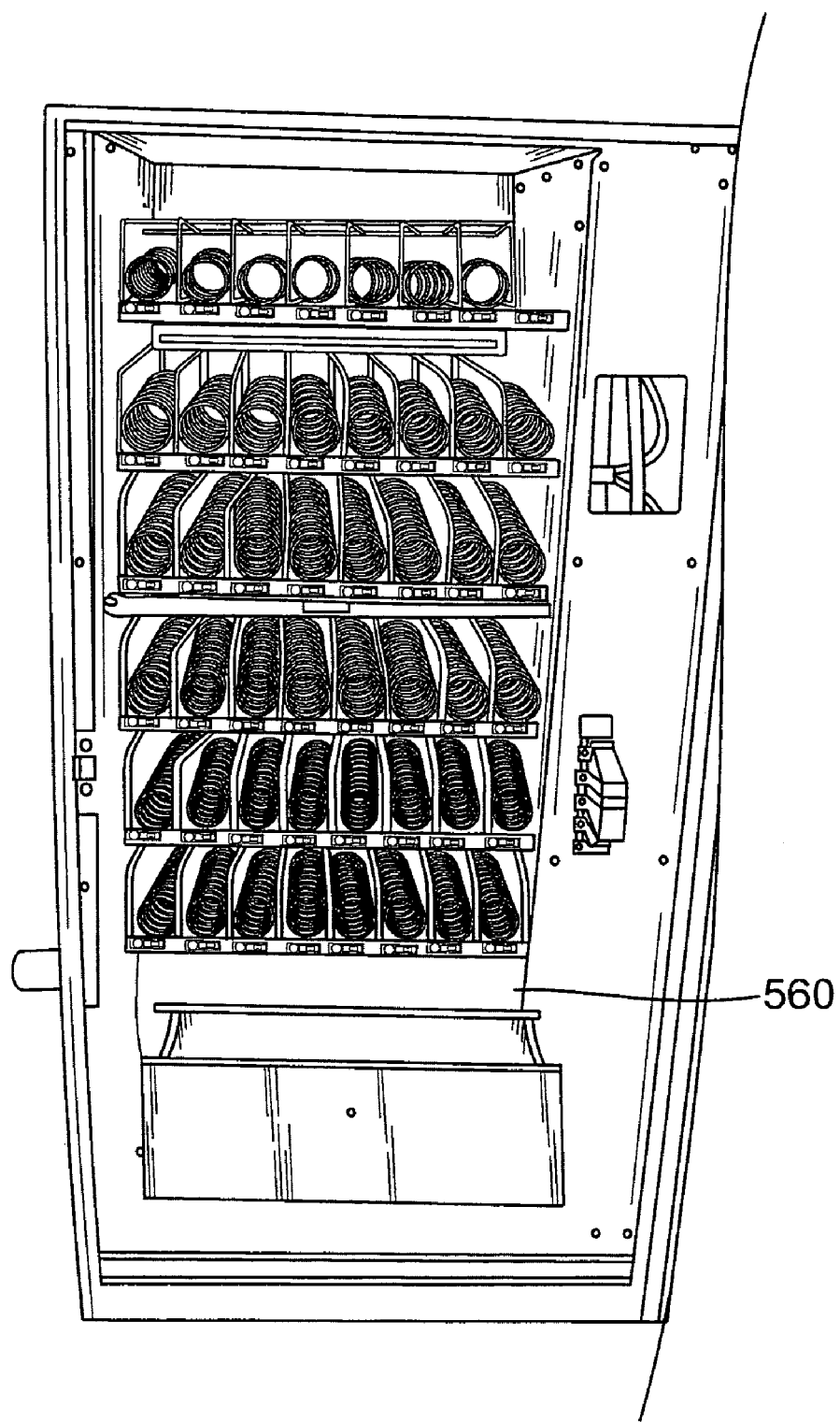
FIG. 5 is an interior view of one embodiment of the vending machine of the present invention.
Figure 6:
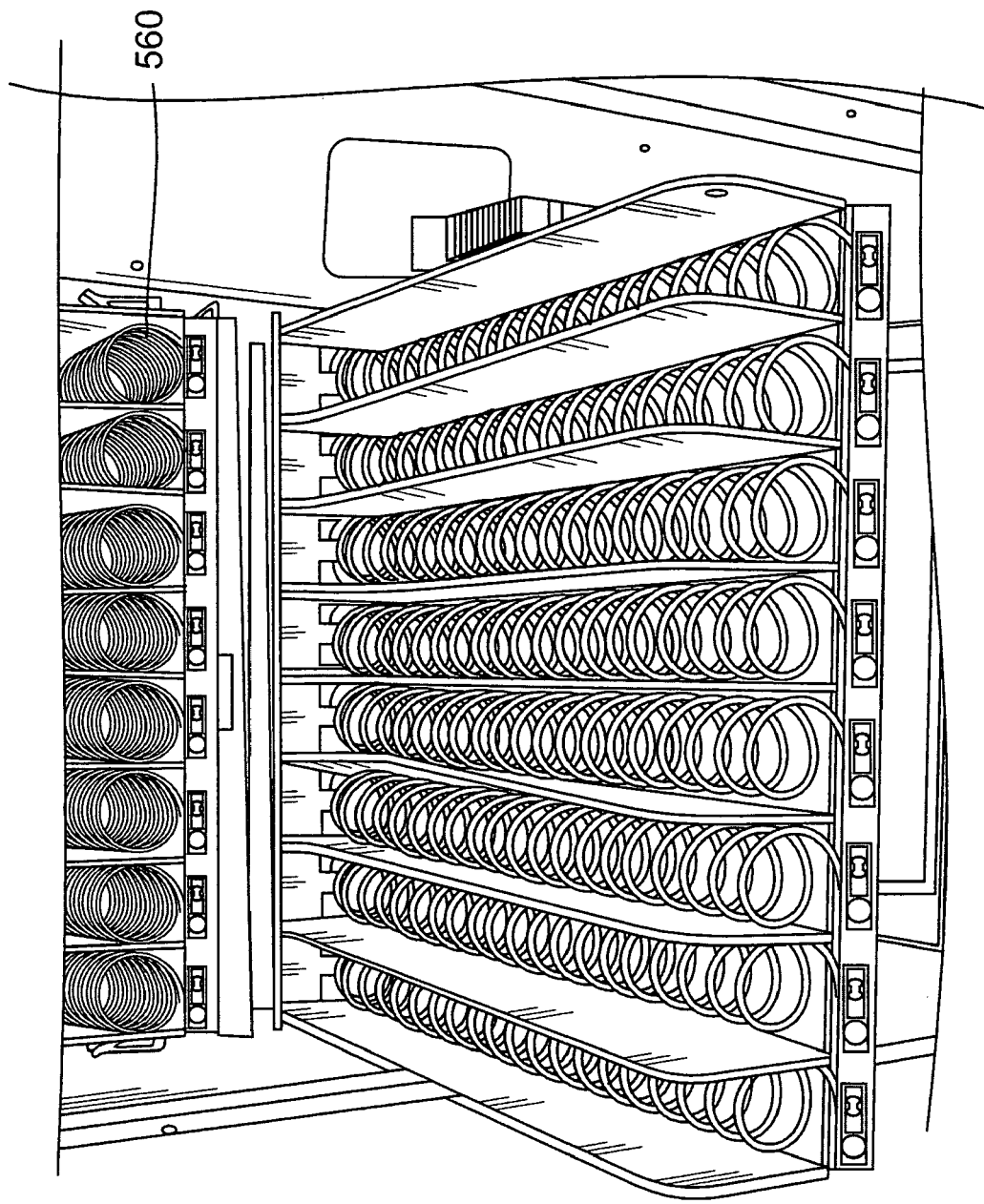
FIG. 6 is an interior view of one embodiment of the vending machine of the present invention with a container tray shown in an extended condition to receive packages of product.

Referring to FIGS. 2 through 6, the present invention encompasses having a separate kiosk vending machine which can be a freestanding vending machine next to which will be posted an armed guard 500 who will be posted 24 hours a day or alternatively inside a store front where there will also be an armed guard 500. The kiosk vending machine 10 will have a selection of the specific medical substances. By way of example, there are six selection buttons 12, 14, 16, 18, 20 and 22 (in the depiction in FIG. 2) which display a specific type of medication and a quantity. It is within the spirit and scope of the present invention to have any number of selection buttons, collectively depicted as 510 in FIG. 4 Each selection button will state the herbal medication or medical substance and the quantity or dose associated with that selection button. It is within the spirit and scope of the present invention to have any multiplicity of buttons for many different types of medical prescription substances in specific quantities. The vending machine will contain a stack of packets of each of the specific medical quantities in the specific amounts. The packets will be retained in trays 560 as illustrated in FIGS. 5 and 6. The kiosk shall have a computer terminal 30 which receives data from the central computer terminal 160 and receives all the information about the specific individual. In addition, an electronic camera 40 will be photographing the individual so that it is clear that the individual that is purchasing the prescription is the same individual who is authorized to do so. Optionally, there will be means 42 for the individual to put in his fingers to confirm that it is the individual who is the person who is purchasing the product and a pin code entry mechanism 50 for the individual to put in his PIN code. Optionally, the PIN code can be input through the selection buttons such as 510. Alternatively, instead of having fingerprints, the individual can have an electronic signature which is placed into the computer 160 and transmitted to the computer 30 and the individual will electronically sign his/her name in an area 42. As an added option, if arrangements have been made for the individual to pay at the kiosk, there will be a payment mechanism 60 which will accept cash or credit cards.

After the individual has been fully verified and has either prepaid for the specific medical substance in the specific quantity and everything has now been determined to be in order by the computer, the individual presses the individual selection button and then the packet of specific medical substance is dispensed into a lower tray 70 which has an opening 72 so that the packet of the substance 74 falls into the tray and the individual can open a door opening 72 and reach in and pull out the substance. Referring to FIGS. 5 and 6, a given row in the tray 560 will move forward and drop the selected packet into the tray.

In another option, the individual will be given a card to be used once to swipe across a credit card reader and this will cause the appropriate packet of medication to be dispensed by the system described above.

Through this method, there is a safe and reliable method for an individual to conveniently purchase the desired quantity of medical substance or herbal substance in a convenient way.

The kiosk can be freestanding and can be positioned at any location on an acceptable sidewalk, comparable to the way drinking dispensing units are placed or within a store as vending machines are placed.

Defined broadly, the vending machine itself will have a display which indicates the specific products that are for sale and the quantities in which such products are being sold. The specific prescription for the individual must list the specific quantity and the specific amount of refills that the individual is allowed for the prescription. The machine will have means by which the critical information of the individual can be put in such as the individual's PIN code and the individual ID program number to correspond to the prescription that has been authorized through the general center. In addition, the machine will have a photo-visual lens to make sure that the individual obtaining the prescription is the same individual to whom the prescription was authorized. Similar to fingerprint scanners used to access information connected to a computer, the machine will have an imprinted signature for the clients to further facilitate them obtaining products without a lengthy waiting process.

Defined more broadly, once the individual is recognized by a photo scanning apparatus in the machine and the individual inserts his proper PIN number and the proper code number and other information that has been provided to the central database to verify that the individual ordering the prescription is in fact the individual who is authorized to obtain the medical substance, then the individual will have either prepaid for the medical substance at the time that the prescription was presented to the central processing agency or will insert a credit card or other payment mechanism to pay for the product which will then be dispensed into a vending tray comparable to the way vending machines presently dispense sodas or candy bars and the individual can then reach into the tray to select the package which contains the appropriate amount of herbal medications or medical substance or other prescribed medication.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A system to enable an individual to legally purchase a medical substance from at least one vending machine, comprising:

a. a central processing center to receive from the individual a prescription from a licensed medical doctor for a specific medical substance in a specific dose and quantity;

b. means at the central processing center to obtain a visual image of the individual;

c. means at the central processing center to fingerprint the individual;

d. means at the central processing center to receive verification information about the individual;

e. means at the central processing center to enable the individual to create a customized PIN code;

f. means at the central processing center to receive payment from the individual;

g. inputting all information received at the central processing center about the individual, comprising the prescription, the visual image, and the fingerprint, the verification information input into a central database which transmits the information through electronic means to at least one vending machine; and h. the at least one vending machine at a location remote from the central processing center, comprising selected quantities of medical substances therein, selection means to select a specific medical substance, means to receive the verification information about the individual from the central database, means at the vending machine to verify the visual image of the individual when the individual is at the at least one vending machine by taking an additional visual image of the individual, means to enable the individual to input the individual's verification information to confirm the identity of the individual, means after confirming the individual's identity to enable the individual to cause the at least one vending machine to dispense the medical substance for which the prescription was obtained and means to enable the individual to receive the medical substance from the vending machine.

2. The apparatus in accordance with claim 1 wherein said verification information includes a driver's license and credit card.

3. A system to enable an individual to legally purchase a medical substance from at least one vending machine, comprising:

a. a central processing center to receive from the individual a legal prescription for a specific substance in a specific dose and quantity;

b. means at the central processing center to obtain a visual image of the individual;

c. means at the central processing center to obtain identification information about the individual and input the information into a central database which transmits the information to the at least one vending machine at a remote location;

d. means to receive payment from the individual; and e. the at least one vending machine at a location remote from the central processing center, comprising selected quantities of medical substances therein, selection means to select a specific medical substance, means to receive the verification information about the individual from the central database, means at the at least one vending machine to verify the visual image of the individual when the individual is at the at least one vending machine by taking an additional visual image of the individual, means to enable the individual to input the individual's verification information to confirm the identity of the individual, means after confirming the individual's identity to enable the individual to cause the at least one vending machine to dispense the medical substance for which the prescription was obtained and means to enable the individual to receive the medical substance from the vending machine.

\* \* \* \* \*